United States Patent [19]

Shutske et al.

[11] Patent Number: 4,994,452
[45] Date of Patent: Feb. 19, 1991

[54] HEXAHYDRO-1H-QUINO[4,3,2-EF][1,4]BENZOXAZEPINES AND RELATED COMPOUNDS

[75] Inventors: Gregory M. Shutske, Somerset; Kevin J. Kapples, Little York, both of N.J.; John D. Tomer, IV, Perkasie, Pa.

[73] Assignee: Hoechst-Roussel Pharmaceuticals Inc., Somerville, N.J.

[21] Appl. No.: 443,288

[22] Filed: Nov. 28, 1989

[51] Int. Cl.$^5$ ............... A61K 31/55; C07D 513/06; C07D 498/06
[52] U.S. Cl. ................ 514/211; 540/544; 540/488; 546/103; 546/105
[58] Field of Search ........... 540/488, 544; 514/211

[56] References Cited

U.S. PATENT DOCUMENTS

| | | | |
|---|---|---|---|
| 3,232,945 | 2/1966 | Sigal et al. | 546/103 |
| 3,318,896 | 5/1967 | Pribyl et al. | 546/105 |
| 3,580,915 | 5/1971 | Wolf et al. | 546/105 |
| 3,987,047 | 10/1976 | Griss et al. | 546/105 |
| 4,631,286 | 12/1986 | Shutske et al. | 546/105 |
| 4,695,573 | 9/1987 | Shutske et al. | 546/105 |
| 4,743,601 | 5/1988 | Shutske et al. | 546/105 |

FOREIGN PATENT DOCUMENTS

| | | | |
|---|---|---|---|
| 0268871 | 6/1988 | European Pat. Off. | 546/105 |
| 8902739 | 4/1989 | World Int. Prop. O. | 546/105 |
| 8902740 | 4/1989 | World Int. Prop. O. | 546/105 |

OTHER PUBLICATIONS

J. Bielavsky, Collection Czechoslav. Chem. Commun., 42, 2802 (1977).
M. E. Konshin, Khimsko-Farmatsevticheskii Zhurnal, 8, 17, (1974), Translation thereof.
M. E. Konshin, Nauch. Tr. Perm. Farmatseut., In-t, 10, 6 (1976) and Translation thereof.
J. F. Flood, Psychopharmacology, 86, 61 (1985).
G. M. Shutske, J. Medicinal Chemistry, 32, 1805 (1989).
W. M. Cholody, Tetrahedron Letters, 28, 5029 (1987).

*Primary Examiner*—Robert T. Bond
*Attorney, Agent, or Firm*—Raymond R. Wittekind

[57] ABSTRACT

Novel hexahydro-1H-quino[4,3,2-ef][1,4]benzoxazepines and related compounds, intermediates for the preparation thereof, and a method for relieving memory dysfunction, utilizing the compounds are disclosed.

55 Claims, No Drawings

HEXAHYDRO-1H-QUINO[4,3,2-EF][1,4]BENZOXAZEPINES AND RELATED COMPOUNDS

The present invention relates to hexahydroquinobenzoxazepines and related compounds. More particularly, the present invention relates to hexahydro-1H-quino[4,3,2-ef][1,4]benzoxazepines and -thiazepines of formula 1

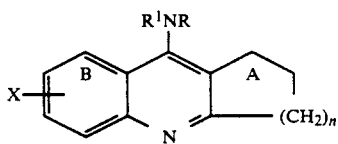

wherein $R^1$ is H, alkyl, or benzyl; R is a group of the formula

wherein Y is H, H or O, $R^2$ is H, alkyl, or phenyl, and Z is O or S; wherein Z of the group of the formula

is bound to either the A- or B-position of the heteroaromatic nucleus; X is H, halogen, alkoxy, alkyl, or trifluoromethyl and n is 1, 2, or 3; the pharmaceutically acceptable salts thereof; and the optical isomers thereof, which are useful for relieving memory dysfunction, for example, memory dysfunction such as that associated with reduced cholinergic function in Alzheimer's disease, alone or in combination with adjuvants.

Subgeneric to the hexahydro-1H-quino[4,3,2-ef][1,4]benzoxazepines and thiazepines of the present invention are compounds wherein:

(a) Z of the group of the formula

is bound to the A-position of the heteroaromatic nucleus; Y is H, H or O and n is 2; and (b) Z of the group of the formula

is bound to the B-position of the heteroaromatic nucleus; Y is H, H or O and n is 2.

The present invention also relates to amines of formula 2

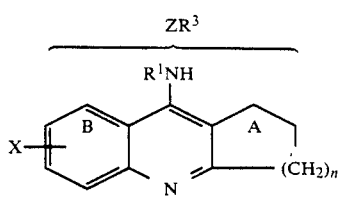

wherein $R^1$ is H, alkyl or benzyl; $R^3$ is a H, alkyl, a group of the formula $CH_2CHR^2Hal$ wherein $R^2$ is hydrogen, alkyl, or phenyl and Hal is chloro, bromo, or iodo, or a group of the formula $CHR^2CO_2R^5$ wherein $R^2$ is as above and $R^5$ is H or alkyl; Z is O or S; X is H, halogen, alkoxy, alkyl, or trifluoromethyl; n is 1, 2, or 3; the group $ZR^3$ is bound to either the A- or B-position of the heteroaromatic nucleus, which are useful as intermediates for the preparation of the present hexahydro-1H-quino[4,3,2-ef][1,4]benzoxazepines and thiazepines and for relieving memory dysfunction.

As used throughout the specification and appended claims, the term "alkyl" refers to a straight or branched chain hydrocarbon radical containing no unsaturation and having 1 to 10 carbon atoms such as methyl, ethyl, n-propyl, tert-butyl, hexyl, octyl, decyl and the like; the term "alkoxy" refers to a monovalent substituent which consists of an alkyl group linked through an ether oxygen and having its free valence bond from the ether oxygen such as methoxy, ethoxy, isopropoxy, tertbutoxy, hexoxy, octoxy, decoxy and the like; the term "halogen" refers to a member of the family fluorine, chlorine, bromine or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by synthesis from optically active precursors.

The present invention comprehends all optical isomers and racemic forms thereof of the compounds disclosed and claimed herein and the formulas of the compounds shown herein are intended to encompass all possible optical isomers of the compounds so depicted.

The novel hexahydro-1H-quino[4,3,2-ef][1,4]benzoxazepines of the present invention are synthesized by the processes illustrated in Reaction Schemes A, B, and C.

To gain entry into the 2,3,4a,5,6,7-hexahydro-1H-quino[4,3,2-ef][1,4]benzoxazepine system, i.e., to elaborate a quinobenzoxazepine 5, a 9-amino-1,2,3,4-tetrahydroacridin-1-ol 3, the synthesis of which is described in G. M. Shutske, et al., Journal of Medicinal Chemistry, 32, 1805 (1989), is condensed with a haloalkanol 9

$$HalCH_2CHR^2OH \quad\quad 9$$

wherein $R^2$ is hydrogen, alkyl, or phenyl and Hal is chloro, bromo, or iodo to provide a 1-(2-haloalkoxy)-1,2,3,4-tetrahydro-9-acridinamine 4 which is cyclized to a 2,3,4a,5,6,7-hexahydrobenzoxazepine 5. See Reaction Scheme A.

The condensation is performed by contacting a tetrahydroacridinol 3 with a haloalkanol 9 in the presence of a mineral acid, for example, hydrochloric acid, hydrobromic acid, sulfuric acid, or nitric acid, or an organic acid, for example methanesulfonic acid, para-toluenesulfonic acid, or trifluoroacetic acid, trifluoroacetic acid being preferred. While the condensation temperature is not narrowly critical, the reaction is preferably performed within the range of about 0° C. to about 50°

C., a reaction temperature of about 25° C. being most preferred.

The cyclization of a 1-(2-haloalkyoxy)acridinamine 4 is carried out in the presence of an alkali metal alkoxide in an ethereal solvent. Among alkali metal alkoxides there may be mentioned lithium, sodium, and potassium methoxide, ethoxide, 1- and 2-propoxide, 1,1-dimethylethoxide, and the like. Potassium 1,1-dimethylethoxide (potassium tertiary-butoxide) is preferred. Among ethereal solvents there may be mentioned diethyl ether, 1,2-dimethoxyethane, dioxane, 2-methoxyethyl ether, and tetrahydrofuran. Tetrahydrofuran is preferred. The cyclization proceeds at a reasonable rate at about 25° C., higher reaction temperatures within the range of about 25° to about 50° C. and lower reaction temperatures within the range of about 0° to 25° C. may be employed. A cyclization temperature of about 25° C. is preferred.

Alternatively, a 2,3,4a,5,6,7-hexahydro-1H-quino[4,3,2-ef][1,4]benzoxazepine 5 is obtained by condensing 3 wherein $R^1$ is hydrogen with an alkyl hydroxyalkanoate of formula 10.

HOCHR²CO₂R⁵         10 wherein $R^2$ is hydrogen, alkyl, or phenyl; and $R^5$ is alkyl, to afford an alkyl [(9-amino-1,2,3,4-tetrahydroacridin-1-yl)oxy]acetate 6 wherein $R^1$ is hydrogen which is cyclized to a 1,3,4a,5,6,7-hexahydrobenzoxazepinone 7 wherein $R^1$ is hydrogen and reduced to a 2,3,4a,5,6,7-hexahydrobenzoxazepine 5 wherein $R^1$ is hydrogen or alkylated to a 1-alkyl-1,3,4a,5,6,7-hexahydro-2H-benzoxazepinone 8 wherein $R^1$ is alkyl and reduced to a 1-alkyl-2,3,4a,5,6,7-hexahydrobenzoxazepine 5 wherein $R^1$ is alkyl.

The condensation is conducted by a process substantially similar to the method hereinbeforedescribed for the conversion of 3 to 4. In this instance, sulfuric acid and a condensation temperature of about 0° C. are the preferred mineral acid and reaction temperature. The condensation is performed in an ethereal solvent such as tetrahydrofuran or neat, i.e., in the absence of a solvent. It is preferred to perform the condensation in the absence of a solvent.

The cyclization of an alkyl [9-aminotetrahydroacridin-1-yl]acetate 6 to a hexahydroquinobenzoxazepinone 7 is also accomplished by the process hereinbeforedescribed for the conversion of 4 to 5.

The reduction is conducted by contacting a hexahydroquinobenzoxazepinone 7 or 8 with an alkali metal aluminum hydride in an ethereal solvent. Included among alkali metal aluminum hydrides are lithium, sodium, and potassium aluminum hydride. Included among ethereal solvents are diethyl ether, 1,2-dimethoxyethane, 2-methoxyethyl ether, dioxane, and tetrahydrofuran. Lithium aluminum hydride and tetrahydrofuran are the preferred reducing agent and solvent, respectively. While the reduction proceeds readily under these conditions, a promoter such as aluminum chloride may be utilized. The reduction also proceeds readily at about 25° C. Elevated temperatures within the range of about 25° to 50° C. and reduced temperatures within the range of about 0° to about 25° C. may be employed.

Similarly, a 2,3,4a,5,6,7-hexahydroquinobenzthiazepine 15 wherein $R^1$ is hydrogen is fabricated by condensing an aminoacridinol 3 wherein $R^1$ is hydrogen with an alkyl thioglycolate of formula 11

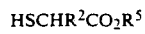

HSCHR²CO₂R⁵         11 wherein $R^2$ is hydrogen, alkyl, or phenyl; and $R^5$ is alkyl to provide an alkyl [(9-amino-1,2,3,4-tetrahydroacridin-1-yl)thio]acetate 12 wherein $R^1$ is hydrogen which is cyclized to a 1,3,4a,5,6,7-hexahydrobenzthiazepinone 13 wherein $R^1$ is hydrogen and reduced to a 2,3,4a,5,6,7-hexahydrobenzthiazepinone 15 wherein $R^1$ is hydrogen by utilizing processes substantially similar to those employed for the conversion of 3 to 8 via 6 and 7. A 2,3,4a,5,6,7-hexahydroquinobenzothiazepine 15 wherein $R^1$ is alkyl is prepared by alkylation of 1,3,4a,5,6,7-hexahydrobenzthiazepine 13 wherein $R^1$ is hydrogen to a 1-alkyl-1,3,4a,5,6,7-hexahydro-2H-benzthiazepin-2-one 14 wherein $R^1$ is alkyl followed by reduction to a 1-alkyl-2,3,4a,5,6,7-hexahydro-1H-benzthiazepine 15 wherein $R^1$ is alkyl by processes also substantially similar to those described for the conversion of 7 to 8 to 5 of Scheme A. See Reaction Scheme B.

The hydrolysis of a benzthiazepinone 13 to [(tetrahydroacridinyl)thio]acetic acid 16 is effected by conventional methods. For example, treatment of an aqueous solution of a benzthiazepinone 13 with hydrochloric acid at ambient temperature gave an acid 16. See Reaction Scheme B.

To gain entry into the 1,3,9,10,11,12-hexahydro-1H-quino[4,3,2-ef][1,4]benzoxazepine system, i.e., to construct a quinobenzoxazepine 21, an 8-hydroxy-1,2,3,4-tetrahydro-9-acridinamine 17 is condensed with an alkyl haloalkanoate 22

HalCHR²CO₂R⁵         22 wherein $R^2$ and $R^5$ are as hereinbeforedescribed and Hal is bromo, chloro, or iodo to yield an alkyl [(9-amino-1,2,3,4-tetrahydroacridin-8-yl)oxy]acetate 18 which is cyclized to a 1,3,9,10,11,12-hexahydro-2H-quino[4,3,2-ef][1,4]benzoxazepin-2-one 19 and either reduced to a 2,3,9,10,11,12-hexahydro-1H-quino[4,3,2-ef][1,4]benzoxazepine 21 wherein $R^1$ is hydrogen or first alkylated to a 1-alkyl-1,3,9,10,11,12-hexahydro-2H-quino[4,3,2-ef][1,4]benzoxazepin-2-one 20 and then reduced to a 2-alkyl-2,3,9,10,11,12-hexahydro-1H-quino[4,3,2-ef][1,4]benzoxazepine 21 wherein $R^1$ is alkyl. See Reaction Scheme C.

The condensation is accomplished by contacting a hydroxyacridinamine 17 with a alkyl haloalkanoate 22 in the presence of an alkali metal carbonate or bicarbonate condensing agent such as, for example, lithium, sodium, or potassium carbonate or bicarbonate in a dipolar aprotic solvent such as, for example, dimethylacetamide, dimethylformamide, hexamethylphosphoramide or dimethylsulfoxide to provide a [(tetrahydroacridinyl)oxy]acetate 18. Potassium carbonate and dimethylformamide are the preferred condensing agent and solvent. The condensation proceeds at a reasonable rate at about 25° C. Higher reaction temperatures (about 25° to about 50° C.) and lower reaction temperatures (about 0° to about 25° C.) may be utilized.

The cyclization of a [(tetrahydroacridinyl)oxy]acetate 18 to a hexahydroquinobenzoxazepinone 19 is effected by processes essentially the same as those hereinbeforedescribed for the cyclization of 4 to 5.

Likewise, the reduction of a hexahydroquinobenzoxazepinone 19 to a 2,3,9,10,11,12-hexahydroquinobenzoxazepinone 21 ($R^1$ is hydrogen) or the reduction of a 2-alkylhexahydroquinobenzoxazepinone 20 to a 2-alkyl-2,3,9,10,11,12-hexahydro-1H-quinobenzoxazepine 21

($R^1$ is alkyl of benzyl) is accomplished by methods essentially the same as those employed for the reduction of 7 to 8. Alternatively, the reductions of 19 to 21 and 20 to 21 are accomplished by diborane in an ethereal solvent, e.g., tetrahydrofuran, 2-methoxyethyl ether or dioxane, at a reduction temperature of from about 0° to about 50° C. Tetrahydrofuran and a reaction temperature of about 25° C. are preferred.

The alkylation is conducted by contacting a hexahydroquinobenzoxazepinone 19 with a haloalkane of formula 23

$$HalR^1 \qquad 23$$

wherein $R^1$ is an hereinbeforedefined in an ethereal solvent, namely, diethyl ether, 2-methoxyethyl ether, 1,2-dimethoxyethane, dioxane or tetrahydrofuran, or a dipolar aprotic solvent, namely dimethylformamide, dimethylacetamide, hexamethylphosphoramide or dimethylsulfoxide, in the presence of a base, namely, an alkali metal alkoxide such as lithium, sodium or potassium methoxide, ethoxide, 1- or 2-propoxide or 1,1-dimethylethoxide. The preferred solvents are tetrahydrofuran and dimethylsulfoxide. The preferred alkali metal alkoxide is potassium 1,1-dimethyethoxide (potassium tertiary-butoxide). The reduction is carried out at a temperature between about 0° to about the reflux temperature of the reaction mixture. When tetrahydrofuran is used as the solvent, it is preferred to perform the alkylation at either about 25° C. or about the reflux temperature of the reaction mixture. When dimethylformamide is employed, it is preferred to carry out the alkylation at about 25° C.

A 2,3,4a,5,6,7-hexahydro-1H-quino[4,3,2-ef][1,4]benzoxazepine 5 is also prepared by the process outline in Reaction Scheme D. For example, treatment of 9-amino-3,4-dihydroxyacridin-1(2H)one 27 ($R^1$ and X are hydrogen), the preparation of which is described in U.S. Pat. No. 4,631,286, issued Dec. 23, 1986, with the styrene oxide in dimethylformamide provides 3,4-dihydro-9-[(2-hydroxy-2-phenyethyl)amino]-1(2H)acridinone 28 ($R^1$ and X are hydrogen and $R^2$ is phenyl), which is reduced with lithium aluminum hydride to 1,2,3,4-tetrahydro-9-[(2-hydroxy-2-phenylethyl)amino]-1-acridinol 29 ($R^1$ and X are hydrogen and $R^2$ is phenyl) and cyclized by means of sulfuric acid/trifluoro acetic acid to 5 ($R^1$ and X are hydrogen and $R^2$ is phenyl.

The starting material for synthesis of the ultimate 2,3,9,10,11,12-hexahydro-1H-quinobenzoxazepines 21, i.e., an 8-hydroxy-1,2,3,4-tetrahydro-9-acridinamine 17, is obtained by condensing a readily available 6-methoxyanthranilonitrile 24 with cyclohexanone 25 in the presence of zinc chloride in nitrobenzene to afford an 8-methoxy-1,2,3,4-tetrahydro-9-acridinamine 26 which is dealkylated to 17 by means of boron tribromide in dichloromethane, as shown below.

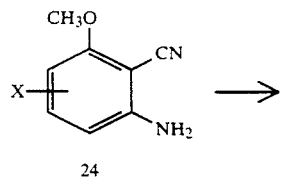
24

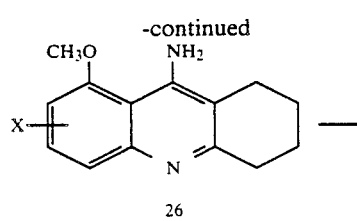
26

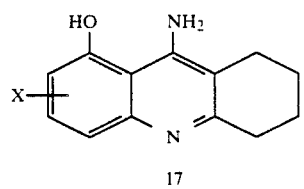
17

The related compounds of the present invention may be prepared from the appropriate precursors by method essentially the same as those hereinbeforedescribed.

The benzoxazepines, -thiazepines, and tetrahydroacridinamines and related compounds of the present invention are useful as agents for the relief of memory dysfunction, particularly dysfunctions associated with decreased cholinergic activity such as those found in Alzheimer's disease. Relief of memory dysfunction activity of the instant compound is demonstrated in the dark avoidance assay, an assay for the determination of the reversal of the effects of scopolamine induced memory deficits associated with decreased levels of acetylcholine in the brain. In this assay, three groups of 15 male CFW mice were used—a vehicle/vehicle control group, a scopolamine/vehicle group, and a scopolamine/drug group. Thirty minutes prior to training, the vehicle/vehicle control group received normal saline subcutaneously, and the scopolamine/vehicle and scopolamine/drug groups received scopolamine subcutaneously (3.0 mg/kg, administered as scopolamine hydrobromide). Five minutes prior to training, the vehicle/vehicle control and scopolamine/vehicle groups received distilled water and the scopolamine/drug group received the test compound in distilled water.

The training/testing apparatus consisted of a plexiglass box approximately 48 cm long, 30 cm high and tapering from 26 cm wide at the top to 3 cm wide at the bottom. The interior of the box was divided equally by a vertical barrier into a light compartment (illuminated by a 25-watt reflector lamp suspended 30 cm from the floor) and a dark compartment (covered). There was a hole at the bottom of the barrier 2.5 cm wide and 6 cm tall and a trap door which could be dropped to prevent an animal from passing between the two compartments. A Coulbourn Instruments small animal shocker was attached to two metal plates which ran the entire length of the apparatus, and a photocell was placed in the dark compartment 7.5 cm from the vertical barrier and 2 cm off the floor. The behavioral session was controlled by PDP 11/34 minicomputer.

At the end of the pretreatment interval, an animal was placed in the light chamber directly under the light fixture, facing away from the door to the dark chamber. The apparatus was then covered and the system activated. If the mouse passed through the barrier to the dark compartment and broke the photocell beam within 180 seconds, the trap door dropped to block escape to the light compartment and an electric shock was administered at an intensity of 0.4 milliamps for three seconds. The animal was then immediately removed from the dark compartment and placed in its home cage. If the animal failed to break the photocell beam within 180 seconds, it was discarded. The latency is seconds for each mouse was recorded.

Twenty-four hours later, the animals were again tested in the same apparatus except that no injections were made and the mice did not receive a shock. The test day latency in seconds for each animal was recorded and the animals were then discarded.

The high degree of variability (due to season of the year, housing conditions, and handling) found in one trial passive avoidance paradigm is well known. To control for this fact, individual cutoff (CO) values were determined for each test, compensating for interest variability. Additionally, it was found that 5 to 7% of the mice in the scopolamine/vehicle control groups were insensitive to scopolamine at 3 mg/kg, sc. Thus, the CO value was defined as the second highest latency time in the control group to more accurately reflect the 1/15 expected control responders in each test group. Experiments with a variety of standards repeated under a number of environmental conditions led to the development of the following empirical criteria: for a valid test, the CO value had to be less than 120 sec and the vehicle/vehicle control group had to have at least 5/15 animals with latencies greater than CO. For a compound to be considered active the scopolamine/compound group had to have at least 3/15 mice with latencies greater than CO.

The results of the dark avoidance test are expressed as the number of animals per group (%) in which this scopolamine induced memory deficit is blocked as measured by an increase in the latency period. Relief of memory dysfunction activity for representative compounds of the present invention is presented in the Table.

TABLE

| Compound | Dose (mg/kg, sc) | Percent of Animals with Scopolamine Induced Memory Deficit Reversal |
|---|---|---|
| 1,3,9,10,11,12-Hexahydro-2H-quino[4,3,2-ef][1,4]benzoxazepin-2-one | 1.0 | 36 |
| 2,3,9,10,11,12-Hexahydro-1H-quino[4,3,2-ef][1,4]benzoxazepine, hydrochloride | 1.0 | 13 |
| 1-Benzyl-1,3,9,10,11,12-hexahydro-2H-quino[4,3,2-ef]-[1,4]benzoxazepin-2-one | 3.0 | 27 |
| 2,3,9,10,11,12-Hexahydro-3-phenyl-1H-quino[4,3,2-ef][1,4]benzoxazepine | 1.0 | 27 |

Included among the compounds of the present inventions are:
a. 1-(2-bromoethoxy)-2,3-dihydro-1H-cyclopenta[b]quinolin-9-amine;
b. ethyl[(11-amino-7,8,9,10-tetrahydro-6H-cyclohepta[b]quinolin-1-yl)oxy]acetate;
c. 2,3,5,6-tetrahydro-1H-4-oxa-1,7-diazanaphth[3,2,1-cd]azulene;
d. 1,9,10,11,12,13-hexahydrocyclohepta[5,6-]pyrido[4,3,2-ef][1,4]benzoxazepin-2(3H)-one;
e. 11-bromo-1,3,4a,5,6,7-hexahydro-2H-quino[4,3,-2ef][1,4]benzoxazepin-2-one;
f. 10-methoxy-1,3,4a,5,6,7-hexahydro-2H-quino[4,3,2-ef][1,4]benzoxazepin-2-one;
g. 2,3,4a,5,6,7-hexahydro-9-methyl-1H-quino[4,3,2-ef][1,4]benzoxazepine; and
h. 2,3,4a,5,6,7-hexahydro-10-trifluoromethyl-1H-quino[4,3,2,ef][1,4]benzoxazepine.

Scopolamine induced memory deficit reversal is achieved when the present benzoxazepines, -thiazepines, tetrahydroacridinamines, and related compounds are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Effective amounts of the compounds of the invention may be administered to a subject by any one of various methods, for example, orally as in capsules or tablets, parenterally in the form of sterile solutions or suspensions, and in some cases intravenously in the form of sterile solutions. The basic final products and intermediates, while effective themselves, may be formulated and administered in the form of their pharmaceutically acceptable acid addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

Similarly, the acidic intermediates may be formulated and administered in the form of their pharmaceutically acceptable base addition salts such as, for example, salts of sodium, potassium, or calcium hydroxide, ammonium hydroxide and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution of suspension. These preparations should contain at least 0.5% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mg of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

1-[(2-Bromoethyl)oxy]-1,2,3,4-tetrahydro-9-acridinamine

To a suspension of 9-amino-1,2,3,4-tetrahydroacridin-1-ol (7.55 g) in 40 ml of 2-bromoethanol was added 9.9 ml of trifluoroacetic acid. The reaction mixture was stirred at ambient temperature for 18 hrs, added to iced sodium hydroxide solution, and the mixture was extracted with ethyl acetate. The combined organic extracts were washed with water, saturated sodium chloride solution, dried over anhydrous magnesium sulfate, filtered, and evaporated. The residue was purified by flash chromatography (ethyl acetate→2% triethylamine/ethyl acetate) to give 7.6 g (67%) of a product. Recrystallization from methanol/water gave the analytical sample, mp 163.5°-164.5° C.

Analysis: Calculated for $C_{15}H_{17}BrN_2O$: 56.08% C, 5.34% H, 8.72% N. Found: 56.27% C, 5.33% H, 8.63% N.

EXAMPLE 2

2,3,4a,5,6,7-Hexahydro-1H-quino-[4,3,2-ef][1,4]benzoxazepine hydrochloride

To a solution of 1-[(2-bromoethyl)oxy]-1,2,3,4-tetrahydro-9-acridinamine (4.1 g) in tetrahydrofuran (30 ml) was added potassium t-butoxide (1.72 g). The reaction mixture was stirred at ambient temperature for 30 mins and then concentrated. The residue was partitioned between water and ethyl acetate and the aqueous phase was extracted twice with ethyl acetate. The combined organic extracts were washed with water, dried over anhydrous magnesium sulfate, filtered, and the filtrate was concentrated to give 2.85 g (92% of basic product. The basic product was dissolved in methanol and treated with ethereal hydrogen chloride. Ether was added. The precipitate was collected and recrystallized from methanol/ethyl ether to give product, m.p. 242°-244° C. (dec.).

Analysis: Calculated for $C_{15}H_{16}N_2O.HCl$: 65.09% C, 6.19% H, 10.12% N. Found: 64.76% C, 6.17% H, 10.08% N.

EXAMPLE 3

9-Benzylamino-1-[(2-bromethyl)oxy]-1,2,3,4-tetrahydroacridine

To a suspension of 9-benzylamino-1,2,3,4-tetrahydroacridin-1ol (7.20 g) in 2-bromoethanol (45 ml) was added 40 drops of trifluoroacetic acid. The reaction mixture was stirred at ambient temperature for 20 mins, added to iced sodium bicarbonate solution, and the suspension was extracted with ethyl acetate. The combined organic extracts were washed with water, saturated sodium chloride solution, dried over anhydrous magnesium sulfate, filtered, and evaporated. The residue was purified by flash chromatography (ethyl acetate→1% triethylamine/ethyl acetate) to give 6.85 g (71%) of product. Recrystallization from cyclohexane gave the analytical sample, mp 89°-91° C.

Analysis: Calculated for $C_{22}H_{23}BrN_2O$: 64.24% C, 5.64% H, 6.81% N. Found: 64.23% C, 5.65% H, 6.77% N.

EXAMPLE 4

1-Benzyl-2,3,4a,5,6,7-hexahydro-1H-quino-[4,3,2-ef][1,4]benzoxazepine fumarate

To a solution of 9-benzylamino-1-[(2-bromoethyl)oxy]-1,2,3,4-tetrahydroacridine (4.4 g) in tetrahydrofuran (30 ml) was added potassium t-butoxide (1.3 g). The reaction was stirred at ambient temperature for 2 hrs, and then concentrated. The residue was partitioned between water and ethyl acetate and the aqueous phase was extracted twice with ethyl acetate. The combined organic extracts were washed with water, saturated sodium chloride solution, dried over anhydrous magnesium sulfate, filtered, and the filtrate was concentrated. The residue was purified by flash chromatography to give 3.2 g (91%) of product. The product was dissolved in ethyl ether and treated with an ethereal solution of fumaric acid to give the fumarate, mp 180°-182° C. (dec.).

Analysis: Calculated for $C_{22}H_{22}N_2O.C_4H_4O_4$: 69.94% C, 5.8% H, 6.28% N. Found: 69.71% C, 5.82% H, 6.22% N.

EXAMPLE 5

Methyl[(9-amino-1,2,3,4-tetrahydroacridin-1-yl)oxy]acetate

To a suspension of 9-amino-1,2,3,4-tetrahydroacridin-1-ol (28.8 g) and methyl glycolate (81.2 g), cooled in an ice bath, was slowly added conc sulfuric acid (20 ml). Ice-water was added. The mixture was washed with ether, and the aqueous phase basified with sodium hydroxide solution, extracted with ethyl acetate, dried over anhydrous magnesium sulfate, and filtered. The filtrate was concentrated and the residue was purified by flash chromatography (10% triethylamine/toluene) to give 10.9 (28.4%) of product, mp 157°-163° C.

EXAMPLE 6

1,3,4a,5,6,7-Hexahydro-2H-quino[4,3,2-ef][1,4]benzoxazepin-2-one

To a solution of methyl [(9-amino-1,2,3,4-tetrahydroacridin-1-yl)oxy]acetate (13.7 g) in tetrahydrofuran (200 ml) was added potassium t-butoxide (6.7 g). The reaction mixture was stirred at ambient temperature for 2.5 hrs and evaporated. The residue was stirred in dilute potassium carbonate solution/ethyl ether. The precipitate was collected and dried. A 3.5 g sample was recrystallized twice from methanol/water, passed through a column of basic alumina (5% methanol/ethyl acetate) and recrystallized from methanol to give 1.37 g (39%) of product, mp 173°-175° C.

Analysis: Calculated for $C_{15}H_{14}N_2O_2$: 70.85% C, 5.55% H, 11.02% N. Found: 70.90% C, 5.48% H, 10.95% N.

EXAMPLE 7

2,3,4a,5,6,7-Hexahydro-1-methyl-1H-quino[4,3,2-ef][1,4]benzoxazepine maleate hydrate To a solution of 1,3,4a,5,6,7-hexahydro-2H-quino[4,3,2-ef][1,4]-benzoxazepin-2-one (4.09 g) in tetrahydrofuran (100 ml) was added potassium t-butoxide (2.17 g) followed by methyl iodide (1.25 ml). The reaction mixture was stirred in water/ethyl ether, the precipitate was collected and dried to give 2.0 g (46%) of 1,3,4a,5,6,7-hexahydro-1-methyl-2H-quino[4,3,2-ef][1,4]benzoxazepin-2-one.

A solution of lithium aluminum hydride (1M in tetrahydrofuran, 15.0 ml) was diluted with 50 ml of tetrahydrofuran. Aluminum chloride (2.0 g) was added in portions followed by 1,3,4a,5,6,7-hexahydro-1-methyl-2H-quino[4,3,2-ef][1,4]benzoxazepin-2-one (3.35 g). The reaction mixture was stirred for 45 mins and then poured into iced dilute sodium hydroxide solution. The aqueous phase was extracted with ethyl acetate and the combined organic extracts were washed with water, saturated sodium chloride solution, dried over anhydrous magnesium sulfate and filtered. Concentration of the filtrate gave 3.1 g (97%) basic product. The basic product was dissolved in methanol, maleic acid (1.1. eq) was added, followed by ether. The precipitate was recrystallized from methanol/ethyl ether to give product, mp 166°-168° C. (dec.).

Analysis: Calculated for $C_{16}H_{18}N_2O.C_4H_4O_4.H_2O$: 61.84% C, 6.23% H, 7.21%. Found: 61.94% C, 6.11% H, 7.26%.

EXAMPLE 8

Methyl[(9-amino-1,2,3,4-tetrahydroacridin-1yl)thio]acetate

To a suspension of 9-amino-1,2,3,4-tetrahydroacridin-1-ol (8.82 g) and methyl thioglycolate (40 ml) was added 40 drops of sulfuric acid. The reaction mixture was stirred at ambient temperature for 3 hrs, poured into an iced sodium bicarbonate solution, and extracted with ethyl acetate. The combined organic extracts were washed with water, saturated sodium chloride, and dried over anhydrous magnesium sulfate. The filtrate was concentrated in vacuo and the residue was triturated with ethyl ether to give 2.79 g of product, mp 175°-183° C. (dec.). Recrystallization from methanol/water gave the analytical sample, mp 194°-196° C. (dec.)

Analysis: Calculated for $C_{16}H_{18}N_2O_2S$: 63.55% C, 6.00% H, 9.27% N. Found: 63.42% C, 6.00% H, 9.23% n.

EXAMPLE 9

1,3,4a,5,6,7-Hexahydro-2H-quino[4,3,2-ef]]1,4]benzthiazepin-2-one

To a solution of methyl [(9-amino-1,2,3,4-tetrahydroacridin-1-yl)thio]acetate (10.3 g) in tetrahydrofuran (150 ml) was added potassium t-butoxide (4.6 g). The reaction mixture was stirred at ambient temperature for 45 mins and then concentrated. The residue was stirred in water, the solid was collected, and dried. The solid was purified by flash chromatography (ethyl acetate/dichloromethane→5% methanol/dichloromethane) to give 4.1 g (44%) of product, mp 223°-226° C. (dec.). Recrystallization from methanol gave the analytical sample, mp 223.5°-226° C. (dec.).

Analysis: Calculated for $C_{15}H_{14}N_2OS$: 66.64%C, 5.22%H, 10.36%N. Found 66.28%C, 5.13%H, 10.20%N.

EXAMPLE 10

2,3,4a,5,6,7-Hexahydro-1H-quino-[4,3,2-ef][1,4]benzthiazepine

To a solution of lithium aluminum hydride (30 ml of a 1M solution in tetrahydrofuran diluted to 130 ml with tetrahydrofuran) was added aluminum chloride (3.94 g). The mixture was stirred for 30 mins and then 1,3,4a,5,6,7-hexahydro-2H-quino[4,3,2-ef][1,4]benzthiazepin-2-one (6.65 g) was added. The reaction mixture was stirred for 1 hr and then poured into 60 ml of 10% sodium hydroxide solution. The aqueous phase was extracted with ethyl acetate and the combined organic extracts were washed with water, saturated sodium chloride, dried over anhydrous magnesium sulfate, and filtered. The filtrate was preadsorbed on silica and purified by flash chromatography (2% triethylamine/ethyl acetate) to give 3.0 g (48%) of product, mp 171°-175° C. Recrystallization from methanol/water gave the analytical sample, mp 175°-177° C.

Analysis: Calculated for $C_{15}H_{16}N_2S$: 70.27%C, 6.29%H, 10.93%N. Found: 70.25%C, 6.14%H, 10.81%N.

EXAMPLE 11

[(9-Amino-1,2,3,4-tetrahydroacridin-1-yl)thio]acetic acid hydrochloride

In an experiment following the procedure of Example 9, the filtrate was acidified with hydrochloric acid. The solid was collected, washed with water and dried overnight at 60° C. to give 82% yield of product. A portion of the product was dissolved in hot water and concentrated hydrochloric acid (10 ml) was added. The precipitate was collected, washed with water, and dried to give the analytical sample, mp 268°-269° C. (dec).

Analysis: Calculated for $C_{15}H_{16}N_2O_2S.HCl$: 55.46%C, 5.28%H, 8.63%N. Found: 55.31%C, 5.11%H, 8.55%N.

EXAMPLE 12

2,3,4a,5,6,7-Hexahydro-1-methyl-1H-quino-[4,3,2-ef][1,4]benzthiazepine maleate To a mixture of methyl [(9-amino-1,2,3,4-tetrahydroacridin-1-yl)thio]acetate (5.06 g) in tetrahydrofuran (100 ml) was added potassium t-butoxide (2.3 g). The mixture was stirred for 30 mins and methyl iodide (1.6 ml) was added. Stirring was continued for 2 hrs, and the reaction mixture was poured into water. The aqueous phase was extracted three times with ethyl acetate. The combined organic extracts were purified by flash chromatography (ethyl acetate/dichloromethane) to give 3.42 g (72%) of the 1,3,4a,5,6,7-hexahydro-1-methyl-2H-quino-[4,3,2-ef][1,4]benzthiazepin-2-one, mp 241°–245° C. (dec.).

To 1M lithium aluminum hydride in tetrahydrofuran (14.1 ml), diluted with tetrahydrofuran (50 ml) was added aluminum chloride (1.9 g), followed by 1,3,4a,5,6,7-hexahydro-1-methyl-2H-quino-[4,3,2-ef][1,4]benzthiazepin-2-one (3.42 g). After stirring for 1 hr, the reaction mixture was poured into iced sodium hydroxide solution and extracted three times with ethyl acetate. The combined organic extracts were washed with water, saturated sodium chloride solution, and dried over anhydrous magnesium sulfate, filtered and concentrated. The residue was dissolved in methanol and treated with maleic acid (1.1 eq). Crystallization with ethyl ether followed by recrystallization from methanol/ethyl ether gave 3.17 g (73.0%) of product, mp 200°–201° C. (dec).

Analysis: Calculated for $C_{16}H_{18}N_2S \cdot C_4H_4O_4$: 62.15%C, 5.74%H, 7.25%N. Found: 62.07%C, 5.29%H, 7.16%N.

EXAMPLE 13

8-Methoxy-1,2,3,4-tetrahydro-9-acridinamine

6-Methoxyanthranilonitrile (14.0 g) was dissolved in nitrobenzene (150 ml) and cyclohexanone (18.45 g), and freshly fused zinc chloride (25.6 g) was added. The reaction mixture was warmed at 125° C. for 1.5 hr, cooled to room temperature, and poured into ether (1 l). The solid was collected, washed with ether, and distributed between 2-butanone and ammonium hydroxide. The organic phase was washed with brine, dried, filtered, and evaporated. The residue was recrystallized two times from ethyl acetate to give 13.7 g (63.8%), mp 187°–188° C.

Analysis: Calculated for $C_{14}H_{16}N_2O$: 73.66%C, 7.06%H, 12.27%N. Found: 73.77%C, 7.11%H, 12.32%N.

EXAMPLE 14

8-Hydroxy-1,2,3,4-tetrahydro-9-acridinamine hydrochloride

8-Methoxy-1,2,3,4-tetrahydro-9-acridinamine (4.0 g) was dissolved in dichloromethane (76 ml). Boron tribromide in dichloromethane (15.0 ml of a 1.0M solution) was added, and the reaction mixture was stirred 1 hr and then concentrated under reduced pressure. The residue was dissolved in warm water (100 ml), concentrated hydrochloric acid (400 ml) was added and the solution was chilled overnight in the refrigerator. The salt was collected and recrystallized from methanol-ether to give 2.68 g (61%) of product, mp 270° C. (dec).

Analysis: Calculated for $C_{13}H_{14}N_2O \cdot HCl$: 62.27%C, 6.03%H, 11.18%N. Found: 62.35%C, 6.02%H, 11.05%N.

EXAMPLE 15

Ethyl[(9-amino-1,2,3,4-tetrahydroacridin-8-yl)oxy]acetate

8-Hydroxy-1,2,3,4-tetrahydro-9-acridinamine hydrochloride (18.07 g) was suspended in 500 ml of dry dimethylformamide. Potassium carbonate (22.6 g) was added, and the reaction mixture was stirred vigorously for 30 mins. Ethyl bromoacetate (18.0 g) was added dropwise, and the reaction was stirred vigorously overnight. The reaction mixture was distributed between ethyl acetate and water, and the organic layer was separated. The aqueous phase was extracted three times with ethyl acetate, and the combined organic phase was washed with water, dried, filtered, and the filtrate evaporate. The residue was purified by flash chromatography (ethyl acetate, then 5% triethylamine/ethyl acetate) to give 15.75 g (72.91%) of product, mp 141°–142° C.

Analysis: Calculated for $C_{17}H_{20}N_2O_3$: 67.98%C, 6.71%H, 9.33%N. Found: 68.07%C, 6.71%H, 9.26%N.

EXAMPLE 16

1,3,9,10,11,12-Hexahydro-2-H-quino-[4,3,2-ef][1,4]benzoxazepin-2-one

Ethyl[(9-amino-1,2,3,4-tetrahydroacridin-8-yl)oxy]acetate (14.50 g) was dissolved in dry tetrahydrofuran (350 ml) and potassium t-butoxide (6.0 g) was added. After stirring for 1 hr, 100 ml saturated ammonium chloride solution (100 ml) was added, and stirring was continued for 30 min. The reaction mixture was evaporated under reduced pressure. The solid was collected and washed with water to give 10.15 g (82.65%) of product, mp 201°–202° C.

Analysis: Calculated for $C_{15}H_{14}N_2O_2$: 70.85%C, 5.55%H, 11.02%N. Found: 70.91%C, 5.62%H, 10.92%N.

EXAMPLE 17

2,3,9,10,11,12-Hexahydro-1H-quino[4,3,2-ef][1,4]benzoxazepine hydrochloride 1,3,9,10,11,12-Hexahydro-2H-quino[4,3,2-ef][1,4]benzoxazepin-2-one (4.00 g) was suspended in dry tetrahydrofuran (100 ml) and 1M borane/tetrahydrofuran (16.0 ml) was added. After 2 hrs, an additional 30 ml of 1M borane/tetrahydrofuran was added, and the reaction mixture was stirred overnight. The reaction mixture was poured into 5% hydrochloric acid and stirred unit hydrogen evolution ceased. The organic layer was separated and the aqueous phase was washed once with ethyl acetate. The aqueous phase was basified with 10% sodium hydroxide solution and precipitate was collected. The precipitate was treated with methanol/ether/hydrogen chloride. Recrystallized from methanol/ether gave 2.50 g (57.5%) of product, mp 300° C. (dec).

Analysis: Calculated for $C_{15}H_{16}N_2O \cdot HCl$: 65.10%C, 6.19%H, 10.12%N. Found: 64.79%C, 6.22%H, 10.00%N.

EXAMPLE 18

1,3,9,10,11,12-Hexahydro-1-methyl-2H-quino[4,3,2,-ef][1,4]benzoxazepin-2-one

To a suspension of 1,3,9,10,11,12-hexahydro-2H-quino[4,3,2-ef][1,4]benzoxazepin-2-one (4.0 g) in dry tetrahydrofuran (120 ml) was added potassium tert-butoxide (1.94 g). The mixture was stirred at room temperature for 15 mins, iodomethane (1.08 ml) was added, and the reaction mixture was stirred at room temperature overnight. The reaction mixture was concentrated, saturated potassium carbonate solution (150 ml) was added, and mixture was extracted twice with 150 ml portions of ethyl acetate. The organic phase was washed with brine, dried over anhydrous magnesium sulfate, filtered, concentrated. Trituration with diethyl ether/pentane gave 3.47 g (82%) of product. Recrystallization from methanol gave the analytical sample, mp 176.5°–177.5° C.

Analysis: Calculated for $C_{16}H_{16}N_2O_2$: 71.62%C, 6.01%H, 10.44%N. Found: 71.42%C, 6.01%H, 10.38%N.

EXAMPLE 19

2,3,9,10,11,12-Hexahydro-1methyl-1H-quino-[4,3,2-ef][1,4]benzoxazepine

To a solution of lithium aluminum hydride in tetrahydrofuran (1.0M, 15.82 ml) and dry tetrahydrofuran (32 ml) was added aluminum chloride (2.10 g) in portions. The mixture was stirred for five mins, 1,3,9,10,11,12-hexahydro-1-methyl-2H-quino[4,3,2-ef][1,4]benzoxazepin-2-one (4.24 g) was added and the mixture was stirred at room temperature overnight. The reaction mixture was quenched with ethyl acetate (150 ml), 10% sodium hydroxide solution was added, and the organic layer was separated. The organic layer was washed wit brine, dried over anhydrous magnesium sulfate, filtered, and concentrated. The residue was adhered to silica (methanol) and flash chromatographed (30–50% ethyl acetate/Hexane) to yield 3.61 g (89.6%) of product, mp 97°–98° C.

Analysis: Calculated for $C_{16}H_{18}N_2O$: 75.56%C, 7.13%H, 11.01%N. Found: 75.30%C, 7.09%H, 10.94%N.

EXAMPLE 20

1-Ethyl-2,3,9,10,11,12-Hexahydro-1H-quino[4,3,2-ef][1,4]benzoxazepine maleate

To suspension of 1,3,9,10,11,12-hexahydro-2H-quino[4,3,2-ef][1,4]benzoxazepin-2-one (5.0 g) in dry tetrahydrofuran (110 ml) was added potassium tert-butoxide (2.65 g). The mixture was stirred for 20 mins, bromoethane (5.88 ml) was added, and the reaction mixture was refluxed for 6.5 hrs. The reaction mixture was concentrated, diluted with saturated potassium carbonate solution, and extracted with ethyl acetate. The organic extractions were dried over anhydrous magnesium sulfate, filtered, and concentrated. The residue was adhered to silica and flash chromatographed (20% ethyl acetate/hexane) to yield 4.53 g (82%) of 1-ethyl-1,3,9,10,11,12-hexahydro-2H-quino[4,3,2-ef][1,4]benzoxazepin-2-one.

To a solution of lithium aluminum hydride in tetrahydrofuran (1.0M, 14.33 ml) and dry tetrahydrofuran (30 ml) was added aluminum chloride (1.91 g) in portions. The mixture was stirred for five mins, 1-ethyl-1,3,9,10,11,12-hexahydro-2H-quino[4,3,2-ef][1,4]benzoxazepin-2-one (4.04 g) was added, and stirring was continued for two hrs. The reaction mixture was quenched with ethyl acetate (200 ml,) 10% sodium hydroxide solution (200 ml) was added, and the organic layer was separated. The organic layer was dried over anhydrous magnesium sulfate, and concentrated. Recrystallization of the residue from diethyl ether gave 2.41 g (59%) of product, mp 70.5°–72° C. The maleate salt was formed from hot methanol and had mp 188° C. (dec.).

Analysis: Calculated for $C_{17}H_{20}N_2O \cdot C_4H_4O_4$: 65.61%C, 6.29%H, 7.29%N. Found: 65.62%C, 6.19%H, 7.25%N.

EXAMPLE 21

2,3,9,10,11,12-Hexahydro-1-propyl-1H-quino[4,3,2-ef][1,4]benzoxazepine

To a suspension of 1,3,9,10,11,12-hexahydro-2H-quino[4,3,2-ef][1,4]benzoxazepin-2-one (4.94 g) in dry tetrahydrofuran (150 ml) was added potassium tert-butoxide (2.62 g). The mixture was stirred for 15 mins, 1-bromopropane (7.07 ml) was added, and the reaction mixture was refluxed overnight. The reaction mixture was concentrated, diluted with saturated potassium carbonate solution, and extracted with ethyl acetate. The organic extracts were dried over anhydrous magnesium sulfate, filtered, and the filtrate was concentrated. The residue was to adhered to adhered to silica, and flash chromatographed (30% ethyl acetate/hexane). The appropriate fractions were evaporated and the residue was triturated with diethyl ether to yield 4.39 g (76%) of 1,3,9,10,11,12-hexahydro-1-propyl-2H-quino[4,3,2-ef][1,4]benzoxazepin-2-one.

To a solution of lithium aluminum hydride in tetrahydrofuran (1.0M, 14.2 ml) and dry tetrahydrofuran (30 ml) was added aluminum chloride (1.89 g) in portions. The mixture was stirred for five mins, 1,3,9,10,11,12-hexahydro-1-propyl-2H-quino[4,3,2-ef][1,4]benzoxazepin-2-one (4.2 g) was added, and stirring was continued overnight. The reaction mixture was quenched with ethyl acetate (200 ml), 10% sodium hydroxide solution (200 ml) was added, and the organic layer was separated. The organic layer was dried over anhydrous magnesium sulfate, filtered, and the filtrate was concentrated. The residue was recrystallized from pentane/diethyl ether to yield 2.85 g (71%) of product, mp 74.5°–75.5° C.

Analysis: Calculated for $C_{18}H_{22}N_2O$: 76.56%C, 7.85%H, 9.92%N. Found: 76.50%C, 7.88%H, 9.84%N.

EXAMPLE 22

1-Benzyl-1,3,9,10,11,12-hexahydro-2H-quino[4,3,2-ef][1,2]benzoxazepin-2-one

To a suspension of 1,3,9,10,11,12-hexahydro-2H-quino[4,3,2-ef][1,4]benzoxazepin-2-one (4.30 g) in dry dimethylformamide (50 ml) was added potassium tert-butoxide (2.1 g). To the solution was added benzyl bromide (2.22 ml), and stirring was continued for five mins. The reaction mixture was diluted with water (150 ml) and extracted with diethyl ether. The organic phase was washed with water, brine, dried over anhydrous magnesium sulfate, filtered, and the filtrate was concentrated. Trituration of the residue with pentane followed by recrystallization from methanol gave 2.42 g (41%) of product, mp 166°–167.5° C.

Analysis: Calculated for $C_{22}H_{20}N_2O_2$: 76.72%C, 5.85%H, 8.13%N. Found: 76.72%C, 5.92%H, 8.12%N.

EXAMPLE 23

1-Benzyl-2,3,9,10,11,12-hexahydroquino[4,3,2-ef][1,4]benzeoxazepine

To a solution of 1-benzyl-1,3,9,10,11,12-hexahydro-2H-quino[4,3,2-ef][1,4]benzoxazepin-2-one (4.71 g) in dry tetrahydrofuran (200 ml) was added borane in tetrahydrofuran (1M, 65 ml). The reaction mixture was stirred at room temperature overnight, quenched with 5% hydrochloric acid (500 ml), and stirred for an additional 2.5 hrs. The reaction mixture was cooled (0° C.), basified with 10% sodium hydroxide solution (500 ml), and extracted with ethyl acetate (800 ml). The organic phase was washed with brine, dried over anhydrous magnesium sulfate, and concentrated. Recrystallization of the residue from methanol yielded 3.05 g (68%) of product, mp 132°–133° C.

Analysis: Calculated for $C_{22}H_{22}N_2O$: 79.97%C, 6.71%H, 8.48%N. Found: 79.83%C, 6.73%H, 8.47%N.

EXAMPLE 24

1,3,9,10,11,12-Hexahydro-3-methyl-2H-quino[4,3,2-ef][1,4]benzoxazepin-2-one

To a solution of 8-hydroxy-1,2,3,4-tetrahydro-9-acrdinamine hydrochloride (3.77 g) in dry dimethylformamide (100 ml) was added potassium carbonate (4.7 g), with stirring. After one hr, methyl 2-bromopropionate (2.51 ml) was added and stirring was continued overnight. The reaction mixture was diluted with water, extracted with ethyl acetate, dried over anhydrous sodium sulfate, concentrated, and the residue was flash chromatographed (ethyl acetate, then 5% triethylamine/ethyl acetate) to yield 4.05 g (86.7%) of methyl α-[(9-amino-1,2,3,4-tetrahydroacridin-8-yl)oxy]-propionate hydrate.

To a solution of the methyl α-[(9-amino-1,2,3,4-tetrahydroacridin-8-yl)oxy]propionate hydrate (3.7 g) in dry tetrahydrofuran (65 ml) was added potassium t-butoxide (1.62 g). The reaction mixture was stirred at room temperature for one hr, saturated ammonium chloride solution (18.2 ml) was added, and stirring was continued for one hr. The mixture was concentrated. The solution was cooled, the solid was collected, washed with water, and dried to yield 2.90 g (90%) of product, mp 200° C. (dec).

Analysis: Calculated for $C_{16}H_{16}N_2O_2$: 71.62%C, 6.01%H, 10.44%N. Found: 71.78%C, 5.88%H, 10.36%N.

EXAMPLE 25

2,3,9,10,11,12-Hexahydro-3-methyl-1H-quino[4,3,2-ef][1,4]benzoxazepine

To a solution of lithium aluminum hydride in tetrahydrofuran (1M, 15.82 ml) and dry tetrahydrofuran (30 ml) was added aluminum chloride (2.10 g) in portions; with stirring. After 5 mins, 1,3,9,10,11,12-hexahydro-3-methyl-2H-quino[4,3,2-ef][1,4]benzoxazepin-2-one (4.24) was added, and the reaction mixture was stirred at room temperature for four hrs. Ethyl acetate (200 ml) and 10% sodium hydroxide solution (200 ml) were added. The organic phase was separated, dried over anhydrous magnesium sulfate, and concentrated. The residue was adhered to silica and flash chromatographed (5% triethylamine/toluene. The appropriate fractions were concentrated and the residue was triturated with diethyl ether to yield 2.48 g (62%) of product, mp 169°–170.5° C.

Analysis: Calculated for $C_{16}H_{18}N_2O$: 75.56%C, 7.13%H, 11.01%N. Found: 75.57% C, 7.08%H, 10.95%N.

EXAMPLE 26

1,3-Dimethyl-2,3,9,10,11,12-hexahydro-1H-quino[4,3,2-ef][1,4]benzoxazepine

To a suspension of 1,3,9,10,11,12-hexahydro-3-methyl-2H-quino[4,3,2-ef][1,4]-benzoxazepin-2-one (5.0 g) in dry tetrahydrofuran (150 ml) was added potassium t-butoxide (3.15 g), with stirring. After 15 mins, methyl iodide (1.39 ml) was added, and the reaction mixture was stirred at room temperature overnight. Additional methyl iodide (0.4 ml) was added. The reaction mixture was refluxed for two hrs, cooled, and concentrated. Saturated potassium carbonate solution was added and the mixture was extracted with ethyl acetate, dried over anhydrous magnesium sulfate, and filtered. The filtrate was concentrated, and the residue was adhered to silica, and flash chromatographed (30–60% ethyl acetate/hexane). The appropriate fractions were concentrated, and the residue was triturated with diethyl ether to give 4.21 g (80%) of 1,3-dimethyl-1,3,9,10,11,12-hexahydro-2H-quino[4,3,2-ef][1,4]benzoxazepin-2-one.

To a solution of lithium aluminum hydride in tetrahydrofuran (1M, 10.0 ml) and dry tetrahydrofuran (30 ml) was added aluminum chloride (1.86 g) in portions, with stirring. The reaction mixture was stirred for five mins and 1,3-dimethyl-1,3,9,10,11,12-hexahydro-2H-quino[4,3,2-ef][1,4]benzoxazepin-2-one (3.95 g) was added. After stirring for 30 min, ethyl acetate (200 ml) and 10% sodium hydroxide solution (200 ml) were added, and the organic layer was separated, dried over anhydrous magnesium sulfate and concentrated. Recrystallization of the residue from diethyl ether/pentane gave 2.2 g (59%) of product, mp 125°–126.5° C.

Analysis: Calculated for $C_{17}H_{20}N_2O$: 76.09%C, 7.51%H, 10.44%N. Found: 75.85%C, 7.33%H, 10.36%N.

EXAMPLE 27

1-Benzyl-2,3,9,10,11,12-hexahydro-3-methyl-1H-quino[4,3,2-ef][1,4]benzoxazepine To a suspension of 1,3,9,10,11,12-hexahydro-3-methyl-2H-quino[4,3,2-ef][1,4]benzoxazepin-2-one (5.0 g) in dry dimethylformamide (60 ml) was added potassium t-butoxide (3.15 g), with stirring. After 15 mins, benzyl bromide (2.66 ml) was added, and the reaction mixture was stirred for two hrs. The reaction mixture was diluted with water (300 ml), extracted twice with 100 ml-portions of diethyl ether, dried over anhydrous magnesium sulfate, filtered, and concentrated. The residue was adhered to silica and flash chromatographed (10–30% ethyl acetate/hexane). The mixed fractions were flash chromatographed (3% ethyl acetate/dichloromethane), and the appropriate fractions were combined, and concentrated. Trituration of the residue with (1/1-diethyl ether/pentane) gave 4.58 g (68%) of 1-benzyl-3-methyl-1,3,9,10,11,12-hexahydro-2H-quino[4,3,2-ef][1,4]benzoxazepin-2-one.

To a solution of lithium aluminum hydride in tetrahydrofuran (1M, 12.2 ml) and dry tetrahydrofuran (30 ml) was added aluminum chloride (1.62 g) in portions, with stirring. After five mins, 1-benzyl-3-methyl-1,3,9,10,11,12-hexahydro-2H-quino[4,3,2-ef][1,4]benzoxazepin-2-one (4.38 g) was added and stirring was continued overnight. Ethyl acetate (200 ml) and 10% sodium hydroxide solution (200 ml) were added, and the organic layer was separated, dried over anhydrous sodium magnesium sulfate, and concentrated. Recrystallization of the residue from methanol/diethyl ether gave 2.82 g (67%) of product, mp 151.5°–153° C.

Analysis: Calculated for $C_{23}H_{24}N_2O$: 80.20%C, 7.02%H, 8.13%N. Found: 80.25% C, 7.13%H, 8.11%N.

EXAMPLE 28

1-Ethyl-2,3,9,10,11,12-hexahydro-3-methyl-1H-quino[4,3,2-ef][1,4]benzoxazepine To a suspension of 1,3,9,10,11,12-hexahydro-3-methyl-2H-quino[4,3,2-ef][1,4]benzoxazepin-2-one (4.82 g) in dry tetrahydrofuran (150 ml) was added potassium tert-butoxide (2.42 g), with stirring. After 20 mins, bromoethane (5.37 ml) was added, and the reaction mixture was refluxed overnight. The reaction mixture was concentrated, diluted with saturated potassium carbonate solution, and extracted with ethyl acetate. The organic extracts were dried over anhydrous magnesium sulfate, concentrated, and the residue was adhered to silica and flash chromatographed (30% ethyl acetate/hexane). The appropriate fractions were concentrated. Trituration of the residue with diethyl ether/pentane (1/1) gave 4.51 g (85%) of 1-ethyl-3-methyl-1,3,9,10,11,12-hexahydro-2H-quino[4,3,2-ef][1,4]benzoxazepin-2-one.

To a solution of lithium aluminum hydride in tetrahydrofuran (1M, 14.22 ml) and dry tetrahydrofuran (30 ml) was added aluminum chloride (1.90 g) in portions, with stirring. After five mins, 1-ethyl-3-methyl-1,3,9,10,11,12-hexahydro-2H-quino]4,3,2-ef][1,4]benzoxazepin-2-one (4.21 g) was added and stirring was continued for 0.5 hr. The reaction mixture was quenched with ethyl acetate (200 ml) and 10% sodium hydroxide solution (200 ml). The organic layer was separated, dried over anhydrous magnesium sulfate, filtered, and concentrated. Recrystallized of the residue from diethyl ether/pentane gave 2.17 g (54%) of product, mp 101°–103° C.

Analysis: Calculated for $C_{18}H_{22}N_2O$: 76.56%C, 7.85%H, 9.92%N. Found: 76.85%C, 7.99%H, 9.92%N.

EXAMPLE 29

3-Ethyl-1,3,9,10,11,12-hexahydro-2H-quino[4,3,2-ef][1,4]benzoxazepin-2-one

To a solution of 8-hydroxy-1,2,3,4-tetrahydro-9-acridinamine hydrochloride (23.08 g) in dry dimethylformamide was added potassium carbonate (28.75 g), with stirring. After one hr, methyl-2-bromobutyrate (15.89 ml) was added dropwise and stirring was continued overnight. The reaction mixture was diluted with water (1.5 l), and extracted with ethyl acetate (2 l). The organic extracts were dried over anhydrous magnesium sulfate, filtered, and the filtrate was concentrated. The residue was flash chromatographed (ethyl, acetate, 5% triethylamine/ethyl acetate) to yield 30.34 g of ethyl α-[(9-amino-1,2,3,4-tetrahydroacridin-8-yl)oxy]butyrate hydrate.

To a solution of ethyl α-[(9-amino-1,2,3,4-tetrahydroacridin-8-yl)oxy]butyrate hydrate (30.34 g) in dry tetrahydrofuran (370 ml) was added potassium t-butoxide (13 g). The reaction mixture was stirred at room temperature for 1.5 hrs. Saturated ammonium chloride solution (150 ml) was added and stirring was continued for one hr. The mixture was concentrated and the concentrate was cooled. The solid was collected, washed with water, and dried to yield 21.26 g (78%) of product, mp 182°–183° C.

Analysis: Calculated for $C_{17}H_{18}N_2O_2$; 72.32%C, 6.43%H, 9.92%N. Found: 72.32%C, 6.41%H, 9.89%N.

EXAMPLE 30

3-Ethyl-2,3,9,10,11,12-hexahydro-1H-quino[4,3,2-ef][1,4]benzoxazepine fumarate To a solution of lithium aluminum hydride in tetrahydrofuran (1M, 14.8 ml) and dry tetrahydrofuran (30 ml) was added aluminum chloride (1.89 g) in portions, with stirring. After 5 mins, 3-ethyl-1,3,9,10,11,12-hexahydro-2H-quino[4,3,2-ef][1,4]benzoxazepin-2-one (4.0 g) was added, and the reaction mixture was stirred at room temperature overnight. Ethyl acetate (200 ml) and 10% sodium hydroxide solution (200 ml) were added. The organic phase was separated, dried over magnesium sulfate, filtered, and the filtrate was concentrated. The residue was flash chromatographed (5% triethylamine/toluene). The appropriate fractions were concentrated and treated with fumaric acid to give 4.05 g (74%) of product, mp 210° C.

Analysis: Calculated for $C_{17}H_{20}N_2O.C_4H_4O_4$: 65.61%C, 6.29%H, 7.29%N. Found: 65.56%C, 6.27%H, 7.26%N.

EXAMPLE 31

3-Ethyl-2,3,9,10,11,12-hexahydro-1-methyl-1H-quino[4,3,2-ef][1,4]benzoxazepine fumarate To a suspension of 3-ethyl-1,3,9,10,11,12-hexahydro-2H-quino[4,3,2-ef][1,4]benzoxazepin-2-one (5.0 g) in dry tetrahydrofuran (150 ml) was added potassium t-butoxide (3.0 g), with stirring. After 20 mins, methyl iodide (1.66) was added, and the reaction mixture was stirred at room temperature overnight. The reaction mixture was concentrated, diluted with saturated potassium carbonate solution, and extracted with 2-butanone. The organic extracts were dried over anhydrous magnesium sulfate and concentrated. The residue was adhered to silica (methanol) and flash chromatographed (50% ethyl acetate/hexane). The appropriate fractions were concentrated and the residue was triturated with diethyl ether to give 3.59 g (68%) of 3-ethyl-1,3,9,10,11,12-hexahydro-1-methyl-2H-quino[4,3,2-ef][1,4]benzoxazepin-2-one.

To a solution of lithium aluminum hydride in tetrahydrofuran (1M, 11.99 ml) and dry tetrahydrofuran (30 ml) was added aluminum chloride (1.6 g) in portions, with stirring. After five mins, 3-ethyl-1,3,9,10,11,12-hexahydro-1-methyl-2H-quino[4,3,2-ef][1,4]benzoxazepin-2-one (3.55 g) was added, and stirring was continued for 0.5 hr. Ethyl acetate (200 ml) and 10% sodium hydroxide solution (200 ml) were added, the organic layer was separated, dried over anhydrous magnesium sulfate, filtered, and the filtrate was concentrated. The residue was flash chromatographed (1.5% triethylamine/toluene). The appropriate fractions were concentrated and the residue was treated with fumaric acid followed by recrystallization from methanol to give 1.82 g (38%) of product, mp 243° C. (dec.).

Analysis: Calculated for $C_{18}H_{22}N_2O.C_4H_4O_4$: 66.32%C, 6.58%H, 7.03%N. Found: 66.34%C, 6.51%H, 7.01%N.

EXAMPLE 32

Methyl
α-[(9-amino-1,2,3,4-tetrahydroacridin-8-yl)oxy]phenylacetate hydrate

8-Hydroxy-1,2,3,4-tetrahydro-9-acridinamine hydrochloride (2.50 g) was suspended in dry dimethylformamide (20 ml). Potassium carbonate (3.0 g) was added, and the mixture was stirred vigorously for 30 mins. Methyl α-bromophenylacetate (2.10 g) was added dropwise, and the reaction mixture was stirred overnight. Water was added and the precipitate was collected. The residue was purified by flash chromatography (5% triethylamine-ethyl acetate). Evaporation of the appropriate fractions followed by recrystallization of the residue from dichloromethane-pentane gave 2.35 g (65.1%) of product, mp 185° C. (dec).

Analysis: Calculated for $C_{22}H_{22}N_2O_3.0.25\ H_2O$: 72.00%C, 6.18%H, 7.64%N. Found: 72.12%C, 6.28%H, 7.60%N.

EXAMPLE 33

1,3,9,10,11,12-Hexahydro-3-phenyl-2H-quino[4,3,2-ef][1,4]benzoxazepin-2-one

Methyl α-[(9-amino-1,2,3,4-tetrahydroacridin-8-yl]phenylacetate hydrate (5.26 g) was dissolved dry tetrahydrofuran (100 ml) and potassium tert-butoxide (1.70 g) was added. After stirring for 1 hr, saturated ammonium chloride solution (100 ml) was added, and stirring was continued for 30 min. The reaction mixture was evaporated and the solid was collected and washed with water. Recrystallization from dimethylformamide-water gave 3.69 g (77.0%) of product, mp 250° (dec).

Analysis: Calculated for $C_{21}H_{18}N_2O_2$: 76.34%C, 5.49%H, 8.48%N. Found: 76.57%C, 5.50%H, 8.45%N.

EXAMPLE 34

2,3,9,10,11,12-Hexahydro-3phenyl-1H-quino[4,3,2-ef][1,4]benzoxazepine

A solution of lithium aluminum hydride in tetrahydrofuran (1M, 12.0 ml) was added to dry tetrahydrofuran (30 ml) followed by aluminum chloride (1.60 g). The mixture was stirred for 15 mins and 1,3,9,10,11,12-hexahydro-3-phenyl-2H-quino[4,3,2-ef][1,4]benzoxazepine-2-one (3.30 g) was added, with stirring. After 30 mins, 10% sodium hydroxide solution was added, and the mixture was extracted with ethyl acetate. The organic phase was dried over anhydrous magnesium sulfate, filtered, and evaporated. The residue was purified by flash chromatography (5% triethylamine-ethyl acetate). Evaporation of the appropriate fractions followed by recrystallization of the residue from dichloromethane-pentane gave 2.14 g (67.72%) of product, mp 194°–195° C.

Analysis: Calculated for $C_{21}H_{20}N_2O$: 79.72%C, 6.37%H, 8.85%N. Found: 79.67%C, 6.38%H, 8.86%N.

EXAMPLE 35

1,3,9,10,11,12-hexahydro-1-methyl-3-phenyl-2H-quino[4,3,2-ef][1,4]benzoxazepin-2-one 1,3,9,10,11,12-hexahydro-1-methyl-3-phenyl-2H-quino[4,3,2-ef][1,4]benzoxazepine fumarate (4.20 g) was suspended in dry tetrahydrofuran (75 ml), chilled with ice/water, and potassium tert-butoxide (1.50 g) was added. The mixture was stirred for 1 hr, methyl iodide (1.90 g) was added, and the mixture was stirred overnight. The reaction mixture was poured into ammonium chloride solution, and the organic layer was separated. The aqueous phase was extracted with ethyl acetate. The combined organic phase was dried over anhydrous magnesium sulfate, filtered, and the filtrate was evaporated. Recrystallization of the residue from methanol gave 3.37 g (77%) of product, mp 188°–189° C.

Analysis: Calculated for $C_{22}H_{20}N_2O_2$: 76.72%C, 5.85%H, 8.14%N. Found: 76.73%C, 5.89%H, 8.12%N.

EXAMPLE 36

2,3,9,10,11,12-Hexahydro-1-methyl-3-phenyl-1H-quino[4,3,2-ef][1,4]benzoxazepine maleate A solution of lithium aluminum hydride in tetrahydrofuran (1M, 14.0 ml) was added to dry tetrahydrofuran (30 ml) followed by aluminum chloride (1.86 g). The mixture was stirred for 15 mins and 1,3,9,10,11,12-hexahydro-1-methyl-3-phenyl-2H-quino[4,3,2-ef][1,4]benzoxazepin-2-one (4.00 g) was added, with stirring. After 30 mins, 10% sodium hydroxide solution was added, and the mixture was extracted with ethyl acetate. The organic phase was dried over anhydrous magnesium sulfate, filtered, and the filtrate was evaporated. The residue was purified by flash chromatography (5% triethylamine-ethyl acetate). The residue, obtained by evaporation of the appropriate fractions, was treated with fumaric acid in methanol-ether. The solid was collected and recrystallized from methanol-ether to give 4.05 g (56.7%) of product, m.p. 172°–173° C.

Analysis: Calculated for $C_{22}H_{22}N_2O.C_4H_4O_4$: 69.94%C, 5.87%H, 6.27%N. Found: 70.01%C, 5.94%H, 6.25%N.

EXAMPLE 37

1-Benzyl-3-ethyl-2,3,9,10,11,12-hexahydro-1H-quino[4,3,2-ef][1,4]benzoxazepine

To a solution of 3-ethyl-2,3,9,10,11,12-hexahydro-1H-quino[4,3,2-ef][1,4]benzoxazepine (5.0 g) in dry tetrahydrofuran (150 ml) was added potassium t-butoxide (3.0 g). The mixture was stirred for 15 mins, benzyl bromide (3.16 ml) was added, and the reaction mixture was stirred at room temperature overnight. The reaction mixture was heated at reflux for 1.5 hrs, allowed to cool, concentrated and diluted with saturated sodium bicarbonate solution (250 ml). The mixture was extracted twice with ethyl acetate (250 ml), and the organic extracts were dried over anhydrous magnesium sulfate, filtered, and concentrated. Trituration of the residue first with pentane and then diethyl ether, gave 4.65 g (71%) of 1-benzyl-3-ethyl-1,3,9,10,11,12-hexahydro-2H-quino[4,3,2-ef][1,4]benzoxazepin-2-one.

To a solution of lithium aluminum hydride in tetrahydrofuran (1M, 11.75 ml) and dry tetrahydrofuran (30 ml) was added aluminum chloride (1.57 g) in portions. The mixture was stirred for five mins. 1-Benzyl-3-ethyl-1,3,9,10,11,12-hexahydro-2H-quino[4,3,2-ef][1,4]benzoxazepin-2-one (4.37 g) was added and stirring was continued for three hrs. The reaction mixture was quenched with ethyl acetate (200 ml), 10% sodium hydroxide solution (200 ml) was added, and the organic layer was separated, dried over anhydrous magnesium sulfate and concentrated. Trituration of the residue with pentane followed by recrystallization from methanol gave 2.86 g (68%) of product, mp 147.5°–149° C.

Analysis: Calculated for $C_{24}H_{26}N_2O$: 80.41%C, 7.31%H, 7.81%N. Found: 80.55%C, 7.61%H, 7.84%N.

EXAMPLE 38

1,3-Diethyl-2,3,9,10,11,12-hexahydro-1H-quino[4,3,2-ef][1,4]benzoxazepine fumarate To a solution of 3-ethyl-1,3,9,10,11,12-hexahydro-2H-quino[4,3,2-ef][1,4benzoxazepin-2-one (4.98 g) in dry tetrahydrofuran (150 ml) was added potassium t-butoxide (2.26 g). The mixture was stirred for 20 mins, bromoethane (5.0 ml) was added, and the reaction mixture was refluxed overnight. The reaction mixture was concentrated, diluted with sodium bicarbonate solution (250 ml), and extracted twice with ethyl acetate (250 ml). The extracts were dried over anhydrous magnesium sulfate and filtered. The filtrate was concentrated, and the residue was triturated first with pentane and the diethyl ether to give 4.40 g (80.3%) of 1,3-diethyl-1,3,9,10,11,12-hexahydro-2H-quino[4,3,2-ef][1,4benzoxazepin-2-one.

To a solution of lithium aluminum hydride in tetrahydrofuran (1M, 12.87 ml) and dry tetrahydrofuran (30 ml) was added aluminum chloride (1.72 g) in portions. The mixture was stirred for five mins. 1,3-Diethyl-1,3,9,10,11,12-hexahydro-2H-quino[4,3,2-ef][1,4benzoxazepin-2-one (4.17 g) was added and stirring was continued for 1.5 hrs. The reaction mixture was quenched with ethyl acetate (200 ml), 10% sodium hydroxide solution was added and the organic layer was separated. The organic layer was dried over anhydrous magnesium sulfate, filtered, concentrated, and the residue was triturated with pentane to give product. The fumarate was formed with fumaric acid methanol/diethyl ether; yield 3.82 g (69%), mp 194° C. (dec).

Analysis: Calculated for $C_{23}H_{28}N_2O_5$: 66.97% C, 6.84% H, 6.79% N. Found: 67.05% C, 6.82% H, 6.80% N.

EXAMPLE 39

2,3,4a,5,6,7-Hexahydro-3-phenyl-1H-quino[4,3,2-ef][1,4]benzoxazepine hydrochloride To a suspension of sodium hydride (5.6 g) in 300 ml of dimethylformamide was added 9-amino-3,4-dihydroacridin-1(2H)one (24.6 g) followed by styrene oxide (15.9 ml). The mixture was heated at 80° C. for 18 hrs. quenched with water, and the aqueous phase was extracted with ethyl acetate. The organic phase was washed with water, saturated sodium chloride solution, dried over anhydrous magnesium sulfate, and filtered. The filtrate was concentrated. The residue was passed through a column of florisil and then purified by flash chromatography (dichloromethane/acetone, 3/1) to give 9.7 g (25%) of 3,4-dihydro-9-[((2-hydroxy-2-phenyl)ethyl)amino]-1(2H)-acridinone.

To a suspension of 3,4-dihydro-9-[((2-hydroxy-2-phenyl)ethyl)amino]-1(2H)-acridine (4.5 g) in 100 ml of tetrahydrofuran was added a solution of lithium aluminum hydride in tetrahydrofuran (1M, 13.5 ml). After stirring at ambient temperature for 1 hr, the reaction mixture was quenched with water (0.5 ml). The precipitate was collected, washed with warm tetrahydrofuran and the filtrate was concentrated to give 4.05 g (90%) of 1,2,3,4-tetrahydro-9-[((2-hydroxy-2-phenyl)ethyl)amino]-1-acridinol.

A mixture of 1,2,3,4-tetrahydro-9-[((2-hydroxy-2-phenyl)ethyl)amino]-1-acridinol (4.05 g), and 5% sulfuric acid/trifluoroacetic acid solution (50 ml) was stirred for 5 mins. The reaction mixture was quenched with ice-water and neutralized with a 10% sodium hydroxide solution. The aqueous phase was extracted with ethyl acetate and the combined organic phase was washed with water, dried over anhydrous magnesium sulfate, and filtered. The filtrate was concentrated and the residue was purified by flash chromatography (3→5→7% triethylamine/toluene) to give 1.4 g (37%) of a major diastereomer and 0.84 g (22%) of a minor diastereomer. The major isomer was dissolved in methanol and treated with an ethereal hydrogen chloride to give 2.05 g of product, mp 274°-275° C. (dec).

Analysis: Calculated for $C_{21}H_{20}N_2O \cdot HCl$: 71.48% C, 6.00% H, 7.94% N. Found: 71.02% C, 5.92% H, 7.86% N.

The minor isomer was dissolved in methanol and treated with an ethereal hydrogen chloride solution. The salt was crystallized by the addition of ether to give 1.10 g of product, mp: 240° C. dec.

Analysis: Calculated for $C_{21}H_{20}N_2O \cdot HCl \cdot 0.5H_2O$: 69.70% C, 6.13% H, 7.74% N. Found: 69.58% C, 6.12% H, 7.47% N.

REACTION SCHEME A

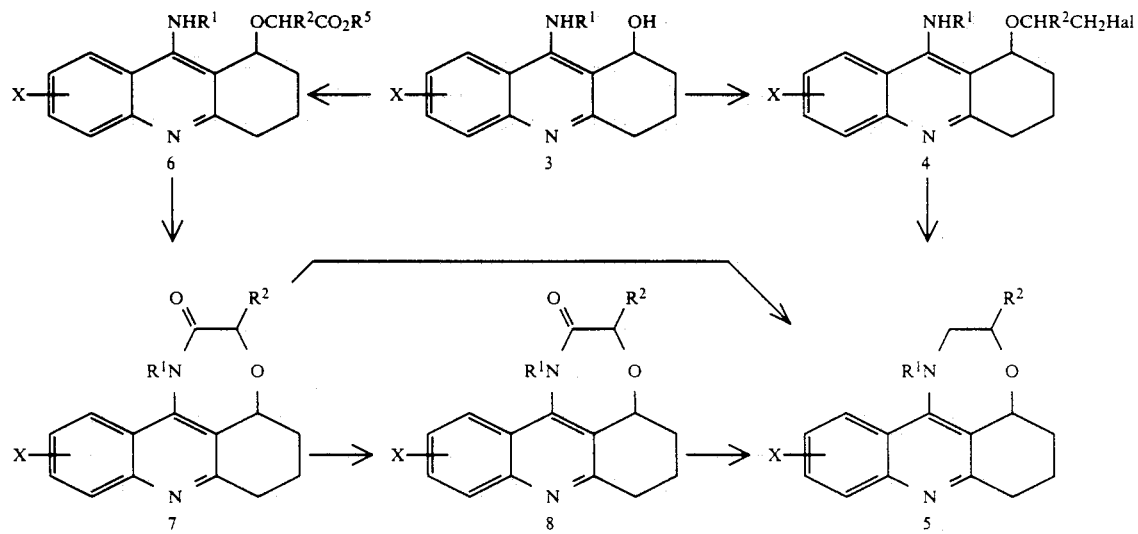

-continued
REACTION SCHEME A
Wherein $R^1$, $R^2$, $R^5$, Hal, and X are as hereinbeforedescribed
REACTION SCHEME B
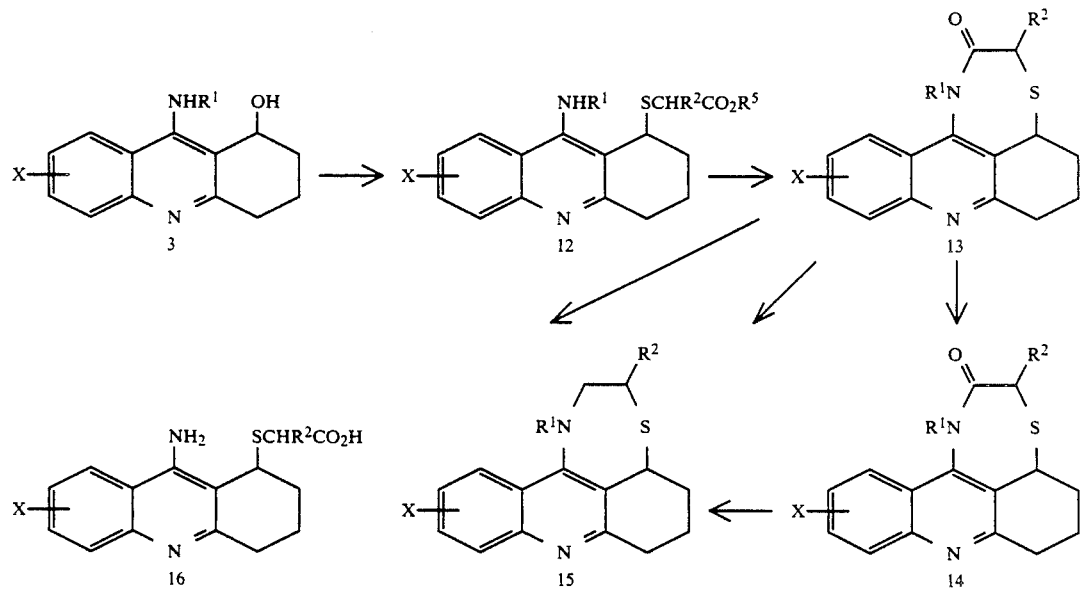
Wherein $R^1$, $R^2$, $R^5$, and X are as hereinbeforedescribed
REACTION SCHEME C
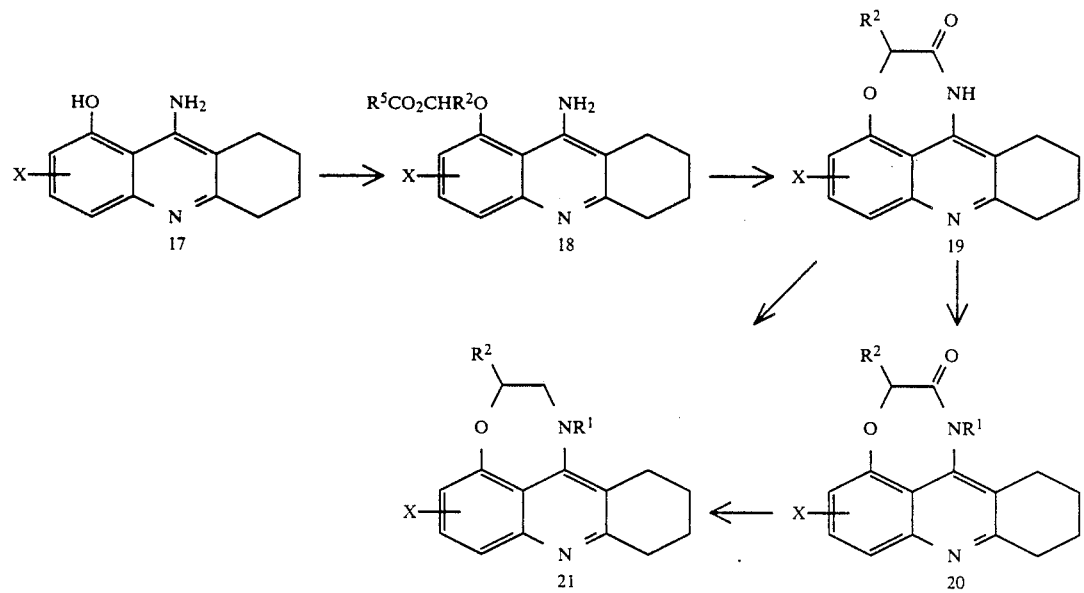
Wherein $R^1$, $R^2$, $R^5$, and X are as hereinbeforedescribed

REACTION SCHEME D

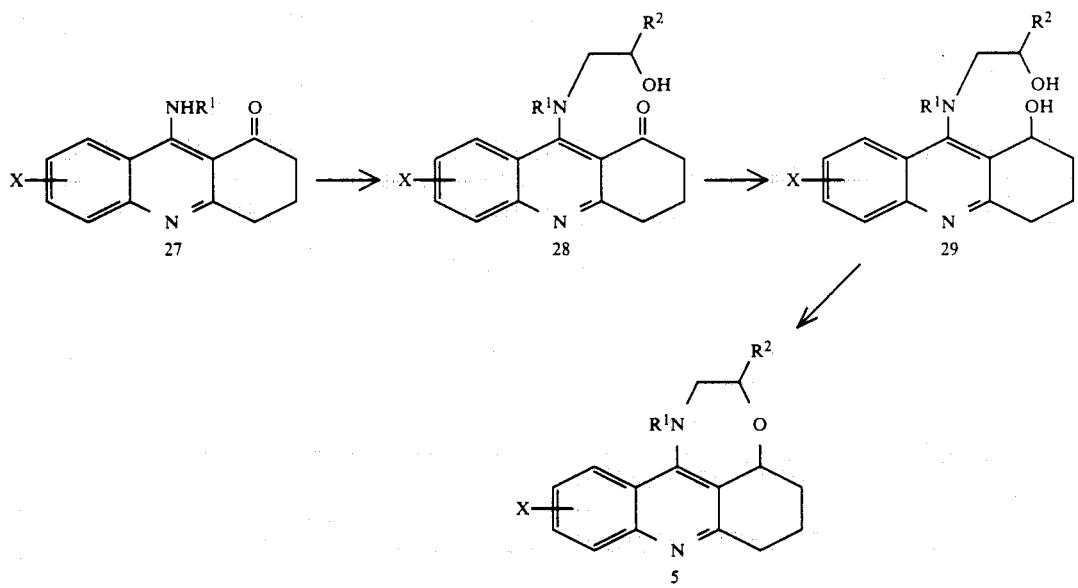

Wherein $R^1$, $R^2$, and X are as hereinbeforedescribed

We claim:
1. A compound of the formula

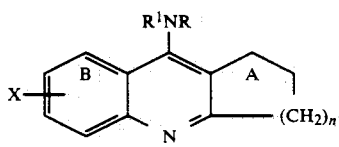

wherein $R^1$ is H, loweralkyl, or benzyl; R is a group of the formula

wherein Y is H, H or O, $R^2$ is H, loweralkyl, or phenyl, and Z is O or S; wherein Z of the group of the formula

is bound to either the A- or B-position of the heteroaromatic nucleus; X is H, halogen, loweralkoxy, loweralkyl, or trifluoromethyl; and n is 1, 2, or 3; the pharmaceutically acceptable salts thereof; and the optical isomers thereof.

2. A compound according to claim 1 wherein Z of the group of the formula

is bound to the A-position of the heteroaromatic nucleus, and n is 2.

3. A compound according to claim 1 wherein Z of the group of the formula

is bound to the B-position of the heteroaromatic nucleus, and n is 2.

4. A compound according to claim 2 wherein Y is H, H.

5. A compound according to claim 2 wherein Y is O.

6. A compound according to claim 3 wherein Y is H, H.

7. A compound according to claim 3 wherein Y is O.

8. The compound according to claim 4 which is 2,3,4a,5,6,7-hexahydro-1H-quino[4,3,2-ef][1,4]benzoxazepine.

9. The compound according to claim 4 which is 1-benzyl-2,3,4a,5,6,7-hexahydro-1H-quino[4,3,2-ef][1,4]benzoxazepine.

10. The compound according to claim 5 which is 1,3,4a,5,6,7-hexahydro-2H-quino[4,3,2-ef][1,4]benzoxazepin-2-one.

11. The compound according to claim 4 which is 2,3,4a,5,6,7-hexahydro-1-methyl-1H-quino[4,3,2-ef][1,4]benzoxazepine.

12. The compound according to claim 5 which is 1,3,4a,5,6,7-hexahydro-2H-quino[4,3,2-ef][1,4]benzthiazepin-2-one.

13. The compound according to claim 4 which is 2,3,4a,5,6,7-hexahydro-1H-quino[4,3,2-ef][1,4]benzthiazepine.

14. The compound according to claim 4 2,3,4a,5,6,7-hexahydro-1-methyl-1H-quino-[4,3,2-ef][1,4]benzthiazepine.

15. The compound according to claim 7 which is 1,3,9,10,11,12-hexahydro-2H-quino[4,3,2-ef][1,4]benzoxazepin-2-one.

16. The compound according to claim 6 which is 2,3,9,10,11,12-hexahydro-1H-quino[4,3,2-ef][1,4]benzoxazepine.

17. The compound according to claim 7 which is 1,3,9,10,11,12-hexahydro-1-methyl-2H-quino[4,3,2-ef][1,4]benzoxazepin-2-one.

18. The compound according to claim 6 which is 2,3,9,10,11,12-hexahydro-1-methyl-1H-quino[4,3,2-ef][1,4]benzoxazepine.

19. The compound according to claim 6 which is 1-ethyl-2,3,9,10,11,12-hexahydro-1H-quino[4,3,2-ef][1,4]benzoxazepine.

20. The compound according to claim 6 which is 2,3,9,10,11,12-hexahydro-1-propyl-1H-quino[4,3,2-ef][1,4]benzoxazepine.

21. The compound according to claim 7 which is 1-benzyl-1,3,9,10,11,12-hexahydro-2H-quino[4,3,2-ef][1,4]benzoxazepin-2-one.

22. The compound according to claim 6 which is 1-benzyl-2,3,9,10,11,12-hexahydro-1H-quino[4,3,2-ef][1,4]benzoxazepine.

23. The compound according to claim 7 which is 1,3,9,10,11,12-hexahydro-3-methyl-2H-quino[4,3,2-ef][1,4]benzoxazepin-2-one.

24. The compound according to claim 6 which is 2,3,9,10,11,12-hexahydro-3-methyl-1H-quino[4,3,2-ef][1,4]benzoxazepine.

25. The compound according to claim 6 which is 1,3-dimethyl-2,3,9,10,11,12-hexahydro-1H-quino[4,3,2-ef][1,4]benzoxazepine.

26. The compound according to claim 6 which is 1-benzyl-2,3,9,10,11,12-hexahydro-3-methyl-1H-quino[4,3,2-ef][1,4]benzoxazepine.

27. The compound according to claim 6 which is 1-ethyl-2,3,9,10,11,12-hexahydro-3-methyl-1H-quino[4,3,2-ef][1,4]benzoxazepine.

28. The compound according to claim 7 which is 3-ethyl-1,3,9,10,11,12-hexahydro-2H-quino[4,3,2-ef][1,4]benzoxazepin-2-one.

29. The compound according to claim 6 which is 3-ethyl-2,3,9,10,11,12-hexahydro-1H-quino[4,3,2-ef][1,4]benzoxazepine.

30. The compound according to claim 6 which is 3-ethyl-2,3,9,10,11,12-hexahydro-1-methyl-1H-quino[4,3,2-ef][1,4]benzoxazepine.

31. The compound according to claim 7 which is 1,3,9,10,11,12-hexahydro-2H-quino[4,3,2-ef][1,4]benzoxazepin-2-one.

32. The compound according to claim 6 which is 2,3,9,10,11,12-hexahydro-3-phenyl-1H-quino[4,3,2-ef][1,4]benzoxazepine.

33. The compound according to claim 7 which is 1,3,9,10,11,12-hexahydro-1-methyl-3-phenyl-2H-quino[4,3,2-ef][1,4]benzoxazepin-2-one.

34. The compound according to claim 6 which is 2,3,9,10,11,12-hexahydro-1-methyl-3-phenyl-1H-quino[4,3,2-ef][1,4]benzoxazepine.

35. The compound according to claim 5 which is 1,3,4a,5,6,7-hexahydro-1-methyl-2H-quino[4,3,2-ef][1,4]benzoxazepin-2-one.

36. The compound according to claim 5 which is 1,3,9,10,11,12-hexahydro-1-methyl-2H-quino-[4,3,2-ef][1,4benzthiazepin-2-one.

37. The compound according to claim 7 which is 2-ethyl-1,3,9,10,11,12-hexahydro-2H-quino[4,3,2-ef][1,4]benzoxazepin-2-one.

38. The compound according to claim 7 which is 1,3,9,10,11,12-hexahydro-1-propyl-2H-quino[4,3,2-ef][1,4]benzoxazepin-2one.

39. The compound according to claim 7 which is 1,3-dimethyl-1,3,9,10,11,12-hexahydro-2H-quino[4,3,2-ef][1,4]benzoxazepin-2-one.

40. The compound according to claim 7 which is 1-benzyl-1,3,9,10,11,12-hexahydro-3-methyl-2H-quino[4,3,2-ef][1,4]benzoxazepin-2-one.

41. The compound according to claim 7 which is 1-ethyl-1,3,9,10,11,12-hexahydro-3-methyl-2H-quino[4,3,2-ef][1,4]benzoxazepin-2-one.

42. The compound according to claim 7 which is 3-ethyl-1,3,9,10,11,12-hexahydro-1-methyl-2H-quino[4,3,2-ef][1,4]benzoxazepin-2-one.

43. A method of relieving memory dysfunction in mammals comprising administering to a mammal memory dysfunction relief, a memory dysfunction relieving effective amount of a compound of claim 1.

44. A memory dysfunction relieving composition comprising and adjuvant and as the active ingredient, a memory dysfunction relieving effective amount of a compound of claim 1.

45. A process for the preparation of a compound of the formula

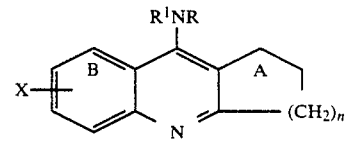

wherein R is a group of the formula

wherein Y is H, H or O, $R^2$ is H, loweralkyl, or phenyl, and Z is O or S; $R^1$ is H, loweralkyl, or benzyl; Z of the group of the formula

is bound to either the A- or B-position of the heteroaromatic nucleus; X is H, halogen, loweralkoxy, loweralkyl, or trifluoromethyl; n is 1, 2, or 3, which comprises contacting a compound of the formula

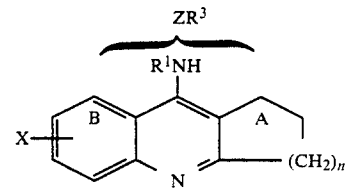

wherein $R^1$ is H, loweralkyl or benzyl; $R^3$ is a group of the formula $CH_2CHR^2Hal$ wherein $R^2$ is hydrogen, loweralkyl, or phenyl and Hal is chloro, bromo, or iodo, or a group of the formula $CHR^2CO_2R^5$ wherein $R^2$ is as above and $R^5$ is H of loweralkyl; Z is O or S; X is H, halogen, loweralkoxy, loweralkyl, or trifluoromethyl; N is 1, 2, or 3; Z of the group $ZR^3$ is bound to either the A- or B-position of the heteroaromatic nucleus with a cyclizing agent.

46. The process of claim 45 wherein the cyclizing agent is an alkali metal alkoxide.

47. The process of claim 46 wherein the alkali metal alkoxide is potassium tertiary butoxide.

48. The process of claim 45 wherein a solvent is employed.

49. The process of claim 48 wherein the solvent is an ethereal solvent.

50. The process of claim 49 wherein the ethereal solvent is tetrahydrofuran.

51. The compound of claim 6 which is 1-benzyl-3-ethyl-2,3,9,10,11,12-hexahydro-1H-quino[4,3,2-ef][1,4]-benzoxazepine.

52. The compound of claim 6 which is 1,3-diethyl-2,3,9,10,11,12-hexahydro-1H-quino[4,3,2-ef][1,4benzoxazepine.

53. The compound of claim 4 which is 2,3,4a,5,6,7-3-phenyl-1H-quino 4,3,2-ef][1,4]benzoxazepine.

54. The compound of claim 7 which is 1-benzyl-3-ethyl-1,3,9,10,11,12-hexahydro-2H-quino[4,3,2-ef][1,4]-benzoxazepin-2-one.

55. The compound of claim 7 which is 1,3-diethyl-1,3,9,10,11,12-hexahydro-2H-quino[4,3,2-ef][1,4]benzoxazepin-2-one.

* * * * *